(12) United States Patent
Staley et al.

(10) Patent No.: US 12,274,841 B2
(45) Date of Patent: Apr. 15, 2025

(54) CATHETER ASSEMBLY

(71) Applicant: Becton, Dickinson and Company, Franklin Lakes, NJ (US)

(72) Inventors: Shaun Staley, Murray, UT (US); Weston Harding, Lehi, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 34 days.

(21) Appl. No.: 16/482,516

(22) PCT Filed: Feb. 24, 2017

(86) PCT No.: PCT/US2017/019430
§ 371 (c)(1),
(2) Date: Jul. 31, 2019

(87) PCT Pub. No.: WO2018/156148
PCT Pub. Date: Aug. 30, 2018

(65) Prior Publication Data
US 2020/0046946 A1 Feb. 13, 2020

(51) Int. Cl.
*A61M 25/00* (2006.01)
*A61M 25/06* (2006.01)

(52) U.S. Cl.
CPC .... *A61M 25/0625* (2013.01); *A61M 25/0097* (2013.01); *A61M 25/0606* (2013.01); *A61M 2025/0076* (2013.01); *A61M 25/0637* (2013.01)

(58) Field of Classification Search
CPC .......... A61M 25/0625; A61M 25/0097; A61M 25/0606; A61M 39/10; A61M 5/34; A61M 2039/1077; A61M 2039/1083; A61M 2039/1088; A61M 5/346; A61M 5/348; A61M 39/24; A61M 2025/0076; A61M 2039/062; A61M 2039/0633; A61M 39/06; A61M 39/0693; A61M 25/0075; A61M 25/003; A61M 25/0618; A61M 5/1626; A61M 2005/1586; A61M 25/0637;
(Continued)

(56) References Cited

U.S. PATENT DOCUMENTS 4,941,881 A * 7/1990 Masters ............ A61M 25/0637 604/162
5,108,376 A * 4/1992 Bonaldo ........... A61M 25/0637 604/110
(Continued)

FOREIGN PATENT DOCUMENTS

CN 202724336 U 2/2013
CN 105396212 A 3/2016
(Continued)

*Primary Examiner* — Shefali D Patel
*Assistant Examiner* — William R Frehe
(74) *Attorney, Agent, or Firm* — Dickinson Wright, PLLC

(57) ABSTRACT

A catheter assembly (10) comprises a catheter (20), a needle (22) having a sharp distal tip and disposed within the catheter (20), a catheter hub (30) connected to the catheter (20) having the needle (22) passing therethrough, and a housing (70) that encloses the sharp distal tip of the needle (22). An external surface of the catheter hub (30) and an internal surface of the housing (70) each include at least one of a channel member (34) and a raised portion (72) that interfit to restrict motion between the catheter hub (30) and the housing (70).

18 Claims, 9 Drawing Sheets

(58) Field of Classification Search
CPC .............. A61M 5/158; A61M 25/0021; A61M 2025/0004; A61M 2025/0175; A61M 25/06

See application file for complete search history.

(56) References Cited

U.S. PATENT DOCUMENTS

| | | | |
|---|---|---|---|
| 5,215,528 | A | 6/1993 | Purdy |
| 5,458,658 | A | 10/1995 | Sircom |
| 7,935,080 | B2 | 5/2011 | Howell |
| 2007/0038187 | A1 | 2/2007 | Albert et al. |
| 2008/0243092 | A1* | 10/2008 | Nilsson ............. A61M 25/0606 604/272 |
| 2011/0060312 | A1* | 3/2011 | Scheurer ............. A61M 39/10 604/523 |
| 2012/0232498 | A1 | 9/2012 | Ma et al. |
| 2012/0277679 | A1* | 11/2012 | Steube ............. A61M 25/0618 604/164.08 |
| 2013/0090607 | A1 | 4/2013 | McKinnon |
| 2013/0090609 | A1 | 4/2013 | Sonderegger et al. |
| 2013/0096504 | A1* | 4/2013 | Walker ............. A61M 25/0618 604/164.08 |
| 2014/0364809 | A1 | 12/2014 | Isaacson et al. |
| 2015/0238733 | A1* | 8/2015 | bin Abdulla ...... A61M 25/0014 604/263 |
| 2015/0306349 | A1 | 10/2015 | Bonnal |
| 2016/0193453 | A1 | 7/2016 | Isaacson et al. |
| 2016/0354580 | A1 | 12/2016 | Teoh |
| 2023/0039751 | A1* | 2/2023 | Shevgoor ............. A61M 5/3293 |

FOREIGN PATENT DOCUMENTS

| | | | |
|---|---|---|---|
| CN | 209286465 U | 8/2019 | |
| EP | 0258566 A2 | 2/1987 | |
| EP | 1683542 A1 | 7/2006 | |
| WO | WO-2015161299 A1 * | 10/2015 | .......... A61M 5/3202 |

\* cited by examiner

CATHETER ASSEMBLY

FIELD

This invention relates to a connection and stabilization mechanism for a catheter assembly.

BACKGROUND

For clinicians to achieve vascular access success when using a catheter assembly, a variety of factors are considered. As catheter assemblies change from using large gauge needles to small gauge needles, stability becomes increasingly difficult to maintain. Improving rigidity and reducing deflection within the catheter assembly provides a clinician improved stability and greater control during insertion. Different features in the catheter assembly can be constrained to minimize motion. However, large features and complex profiles with tight tolerances are difficult to consistently manufacture during production. Also, close circular tolerance fits may not be adequate to sufficiently reduce motion. Further, different insertion techniques can affect stability and control when used by the clinician.

Further stability challenges are encountered in a blood control catheter assembly. An exemplary blood control catheter assembly is disclosed in WO 2015/161294, which is hereby incorporated by reference into this application. Since a valve and a valve actuator are disposed inside a catheter hub, limited space is available inside the catheter hub to provide a stable engagement surface for a needle tip shield or mating components such as a grip or a needle hub. The position of luer threads and appropriate clearance for the luer threads to function properly are additional considerations. Size and shape constraints also factor into creating a more stable and rigid catheter assembly. Thus, a geometrically simple and compact catheter assembly design with increased manufacturability and clinician friendly features is desired.

SUMMARY OF THE INVENTION

It is an aspect of the present invention to provide improved connection features between a catheter hub and a housing, such as a needle protection member, a needle tip shield or mating components such as a grip or a needle hub, in a catheter assembly. The connection features advantageously provide a geometrically simple and compact catheter assembly design that can be manufactured inexpensively and provides stability and rigidity for successful vascular access by a clinician.

The foregoing and/or other aspects of the present invention can be achieved by providing a catheter assembly comprising a catheter, a needle having a sharp distal tip and disposed within the catheter, a catheter hub connected to the catheter having the needle passing therethrough, and a housing for enclosing the sharp distal tip of the needle, wherein an external surface of the catheter hub and an internal surface of the housing each include one of a channel member and a raised portion that interfit to restrict motion between the catheter hub and the housing.

The foregoing and/or other aspects of the present invention can also be achieved by providing a catheter assembly comprising a catheter, a needle having a sharp distal tip and disposed within the catheter, a catheter hub connected to the catheter having the needle passing therethrough, the catheter hub including a valve that selectively permits or blocks a flow of fluid through the catheter, and a valve actuator that moves between a first position and a second position, and a housing that encloses the sharp distal tip of the needle, wherein an external surface of the catheter hub and an internal surface of the housing each include one of a channel member and a raised portion that interfit to limit movement between the catheter hub and the housing.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
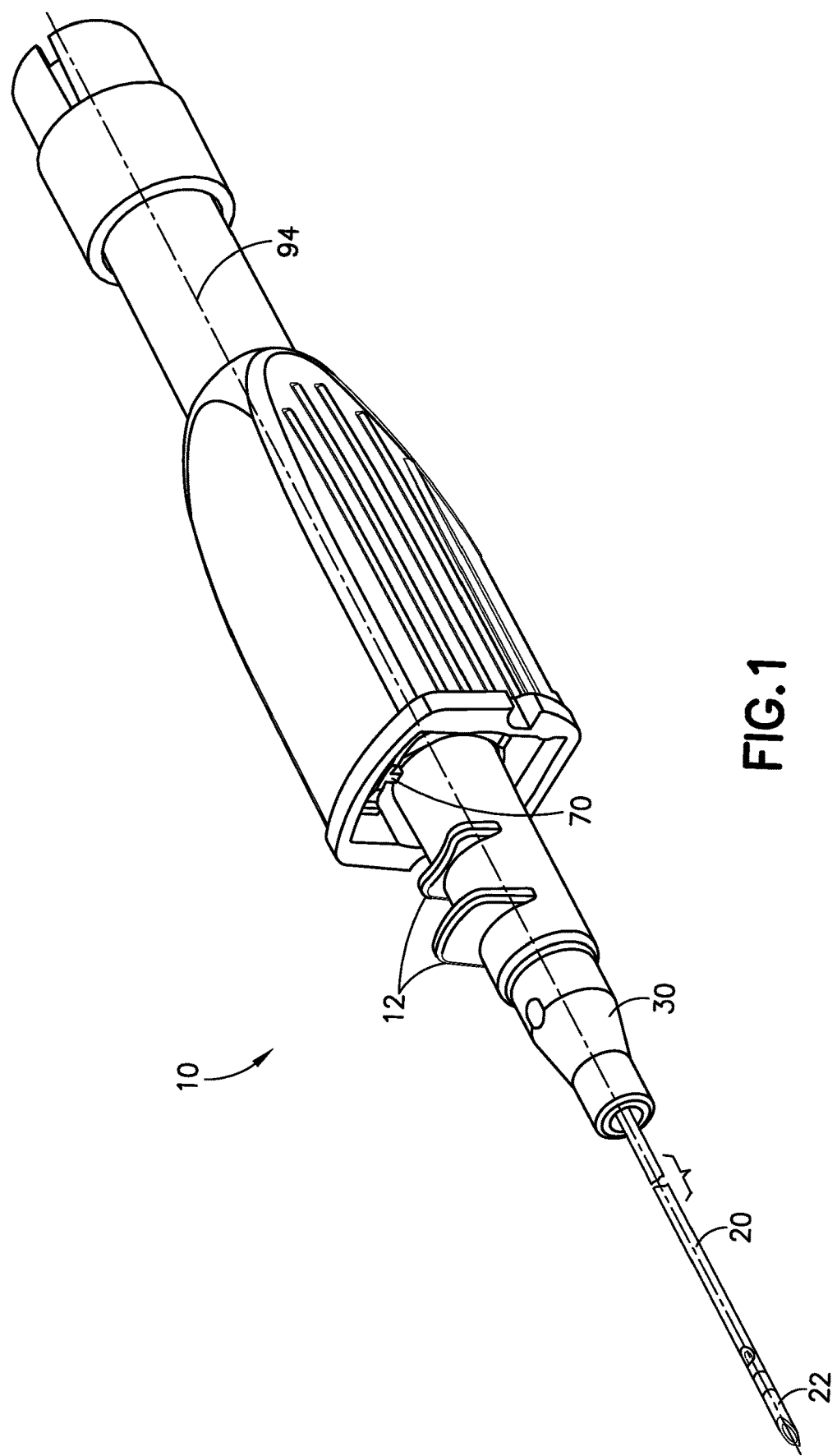
FIG. 1 illustrates a perspective view of a first exemplary embodiment of a catheter assembly.

FIG. 1 illustrates a catheter assembly 10 including a hollow introducer needle 22 disposed in a catheter 20. The needle 22 includes a sharp distal end for insertion into a skin of a patient. During operation, the clinician inserts the needle 22 and the catheter 20 into the patient's skin, but the needle 22 is removed soon after insertion. The catheter 20 remains within the patient's skin for future fluid exchange.

Figure 2:
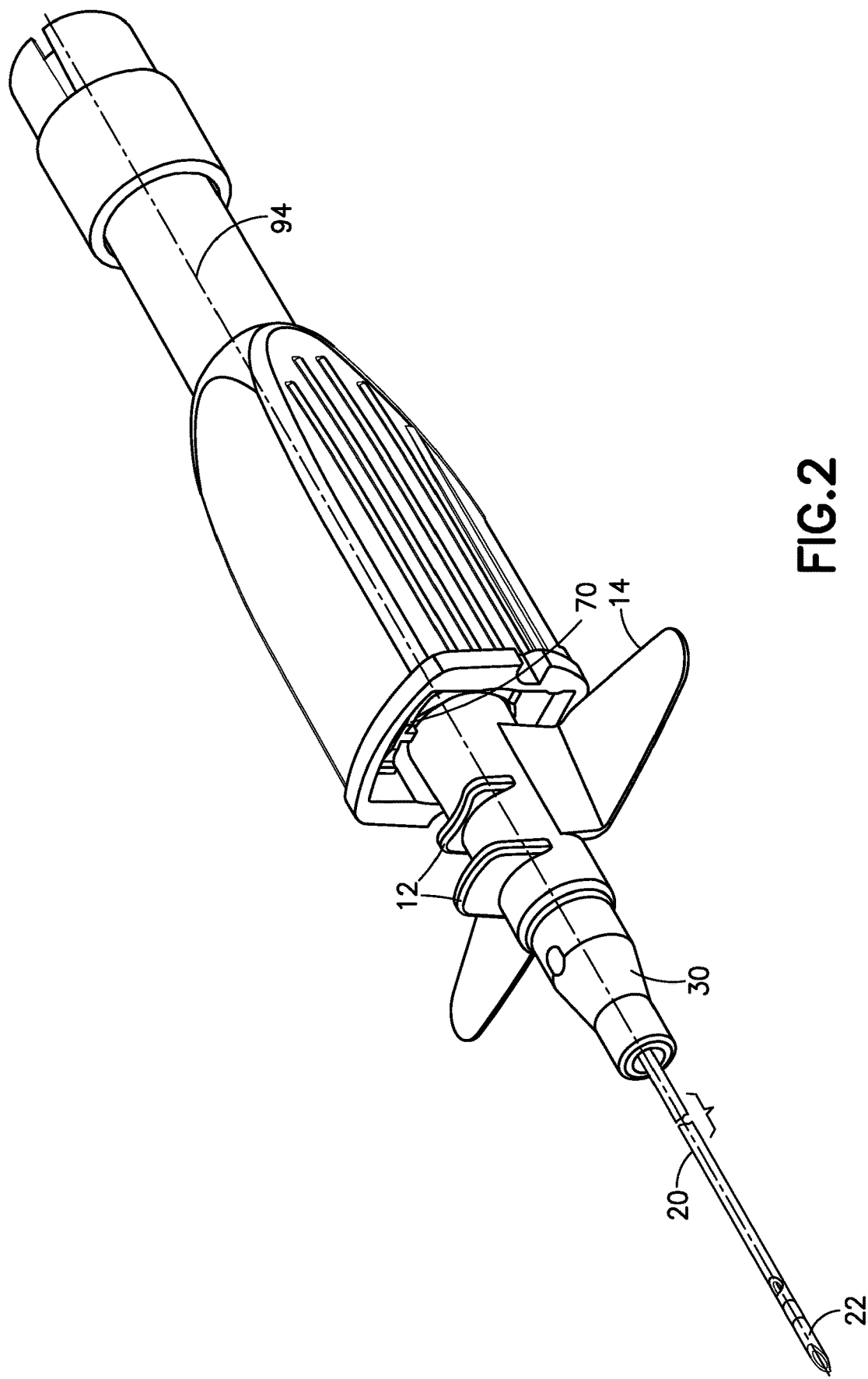
FIG. 2 illustrates a perspective view of a second exemplary embodiment of a catheter assembly including wings.

As illustrated in FIGS. 1 and 2, the catheter 20 is connected to a catheter hub 30. The catheter hub 30 includes one or more finger tabs 12 that are of different heights extending from a top surface. The finger tabs 12 aid the clinician to hold and stabilize the catheter assembly 10 when inserting the needle 22 and catheter 20 into the skin of the patient, as well as to secure the catheter assembly 10 to the patient after catheter 20 insertion.

The catheter hub 30, as illustrated in FIG. 2, can include a pair of wings 14 on opposing sides of the catheter hub 30. Similar to the finger tabs 12, the wings 14 also aid the clinician to hold and stabilize the catheter assembly 10 when inserting the needle 22 and catheter 20 into the skin of the patient, as well as to secure the catheter assembly 10 to the patient after catheter 20 insertion. The wings 14 are secured to the skin of a patient by adhesive, tape or film, for example. Additional features of the catheter hub 30 are described below.

The catheter assembly 10 can further include a needle protection member 70 also known as a needle tip shield. The needle protection member 70 has an internal spring clip 66 that locks the distal end of the needle 22 inside the needle protection member 70. Specifically, the spring clip 66 contacts the side of the needle 22 under a spring force during use. At the same time, the spring clip 66 interlocks with the catheter hub 30 to lock the needle protection member 70 to the catheter hub 30.

In another embodiment, the needle protection member 70 is replaced by mating components such as a grip or a needle hub. These features are all generally identified as a housing 70.

After the needle 22 is used, the distal end of the needle 22 is retracted from the catheter hub 30 and enters into the needle protection member 70. Upon sufficient entrance of the distal end of the needle 22 into the needle protection member 70, a locking action secures the distal end of the needle 22 to prevent further use and needle contamination. In other words, the spring clip 66 is released from the side engagement with the needle 22 to expand and block the movement of the needle 22 back into the catheter hub 30. At the same time, the spring clip 66 disengages from the catheter hub 30 to reverse the interlock between the catheter hub 30 and the needle protection member 70. Additional features of the needle protection member 70 are described below.

Figure 3:
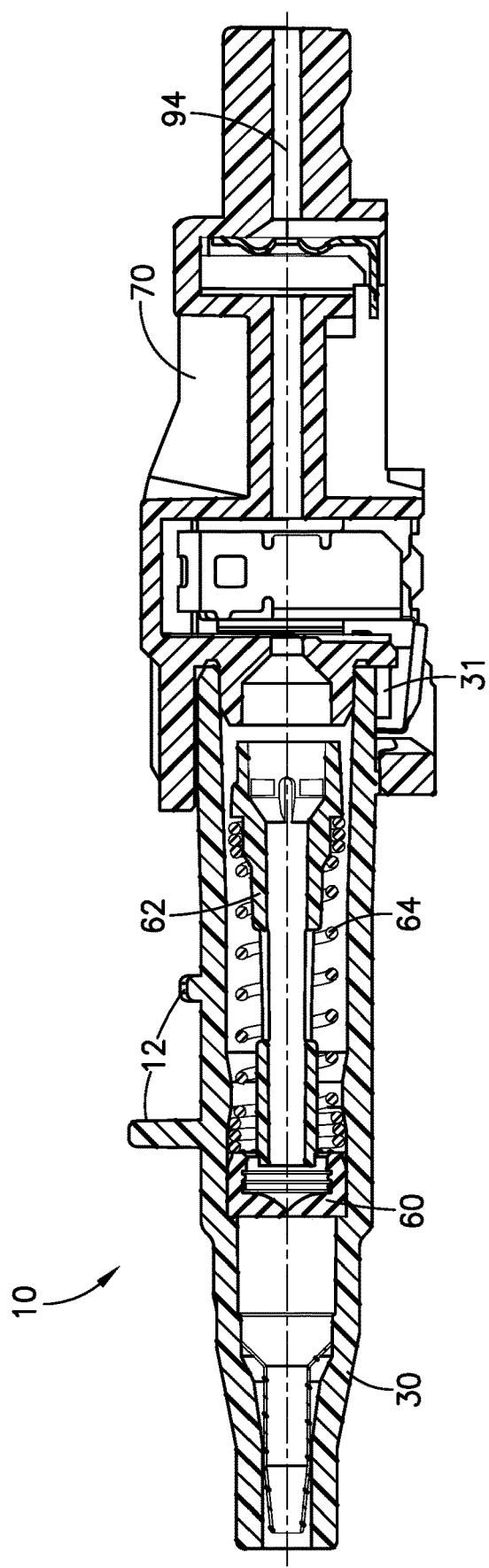
FIG. 3 illustrates a cross sectional view of a third exemplary embodiment of a catheter assembly.

FIG. 3 illustrates a cross sectional view of a typical blood control catheter assembly 10. The features disclosed in this embodiment are similarly present in FIGS. 1 and 2. Specifically, the catheter hub 30 includes a valve 60 that selectively permits or blocks the flow of fluid between the catheter 20 and a distal end of the catheter hub 30. The catheter hub 30 also encloses a valve actuator 62 that selectively penetrates and disengages from the valve 60 to permit or block fluid communication. The valve actuator 62 moves between a first position where the valve 60 is disengaged (closed) and a second position where the valve 60 is penetrated (open).

A return member 64 in the form of a coil spring surrounds the valve actuator 62 and floats within an inner diameter of the catheter hub 30. When the clinician engages and moves the valve actuator 62 to pierce the valve 60 in the second position, the return member 64 urges the valve actuator 62 to disengage the valve 60 and return to the first position. Subsequently, when the clinician disengages the valve actuator 62, the valve actuator 62 moves back to the first position and the valve 60 closes.

The catheter hub 30 includes luer threads 32 and a collar 31 that are disposed at a proximal end of the catheter hub 30. The catheter hub 30 is configured to be selectively engaged and secured to the needle protection member 70 via the spring clip 66 and the collar 31 in the manner described above. The luer threads 32 can be, for example, ISO 80369-7 threads. The luer threads 32 are configured to engage a female connector to exchange fluid, as well as provide rotational stability about the z-axis 94 of the catheter assembly 10. The luer threads 32 are disposed on the sides of the catheter hub 30, whereas the collar 31 is circumferentially disposed on the catheter hub 30. Further details of the components of the catheter hub 30 described in this embodiment are disclosed in WO 2015/161294.

FIGS. 4-9 illustrate the various features of the connection mechanism in the catheter assembly 10 of FIG. 1 between the catheter hub 30 and the needle protection member 70. In view of the problems in the art described above, three main factors have been determined to address and mitigate the concerns of stability and undesired movement in the catheter assembly 10.

The first factor is evaluating the fit between the catheter hub 30 and the needle protection member 70. The closer the fit, the better the assembly is able to minimize undesirable motion. However, requiring tight tolerances in the manufacturing of the catheter hub 30 and the needle protection member 70 is not desired because tight tolerances are difficult to maintain in high volume production.

The second factor is evaluating the distance between two support points in the engagement between the catheter hub 30 and the needle protection member 70 to reduce deflection in the catheter assembly 10. Increasing the distance or length between the support points provides a maximum mechanical or geometric advantage. It is advantageous to position the support points to form a long bearing surface and increase overall stability. Further, the large distance between the support points advantageously results in less free movement and less deflection at the distal tip of the needle. However, size, length and shape constraints limit the available space and amount of possible mechanical advantage that can be designed into the catheter assembly 10.

Figure 5:
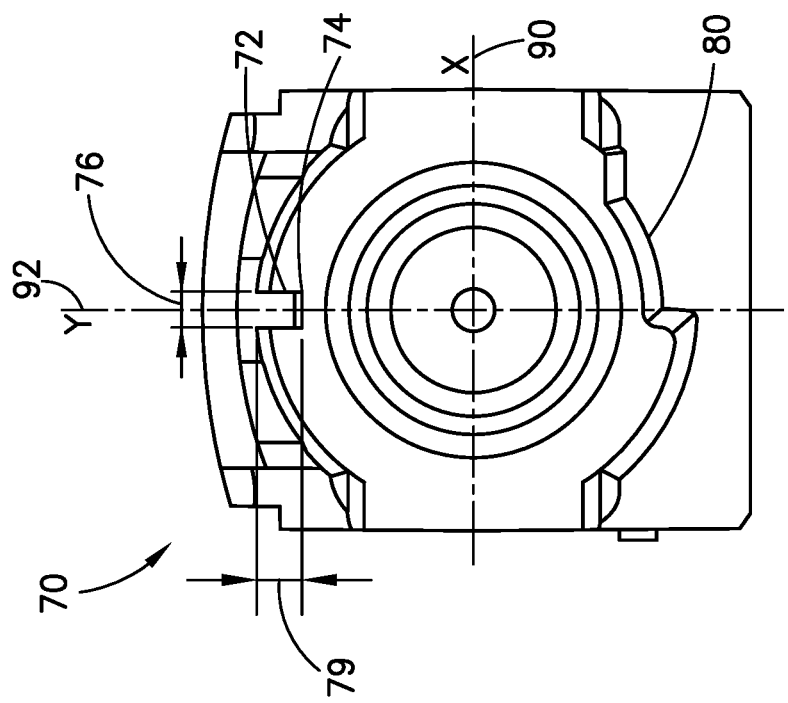
FIG. 5 illustrates a front view of the needle protection member of FIG. 4.

The third factor is evaluating how many degrees of freedom the catheter assembly 10 is constrained by. As illustrated in FIGS. 1-3, the z-axis 94 represents the centerline of the catheter assembly 10. As illustrated in FIG. 5, the x-axis 90 represents the horizontal axis of the catheter assembly 10 and the y-axis 92 represents the vertical axis of the catheter assembly 10. These three axes 90, 92, 94 can be constrained by design in the catheter assembly 10 to restrict motion and improve rigidity during use by the clinician. However, the design challenge is to restrict as much motion as possible using simple and small features that are not difficult to manufacture.

Additional considerations are necessary for a blood control catheter assembly 10. Specifically, as illustrated in FIG. 3, the valve 60 and the valve actuator 62 occupy much of the internal space in the catheter hub 30. Further, a proximal end of the valve actuator 62 is disposed near a proximal end of the catheter hub 30 where the luer threads 32 are located. This positioning allows the valve actuator 62 to be properly engaged by a male luer during operation so that the valve actuator 62 can move between first and second positions to penetrate and disengage the valve 60.

Accordingly, as illustrated in FIG. 3, there is minimal area or length for engagement and internal support at the inner diameter of the catheter hub 30. As a result, a shorter length is available which can decrease the potential mechanical advantage, create a weak and loose engagement, and reduce the stability and rigidity of the catheter assembly. As described below, the features of the presently disclosed connection mechanism remedy the shortcomings of current catheter assemblies.

Figure 4:
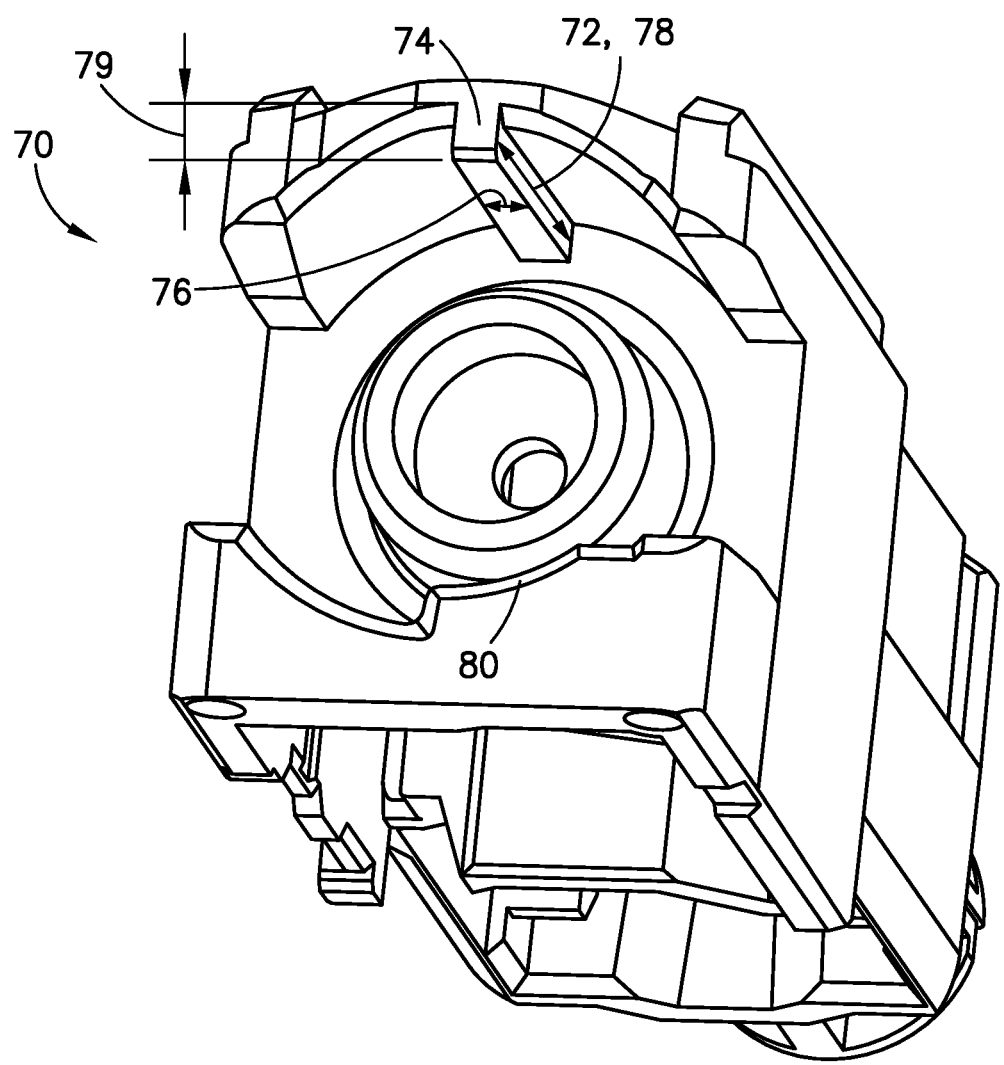
FIG. 4 illustrates a perspective view of a needle protection member of FIGS. 1 and 2.

FIGS. 4 and 5 illustrate the needle protection member 70 or tip shield that encloses and secures a distal end of the needle 22 after use. The needle protection member 70 includes a raised portion 72 disposed at a distal, internal surface. The raised portion 72 is one aspect of the connection mechanism. The raised portion 72 is preferably a rectangular, tongue or rail shaped member that protrudes and extends from the internal surface toward a centerline of the needle protection member 70. The raised portion 72 is preferably disposed at a top surface of the internal surface of the needle protection member 70. It is contemplated, however, that the raised portion 72 can be located at any angular position on the internal surface of the needle protection member 70.

A chamfer 74 is disposed at a distal end of the raised portion 72. The chamfer 74 advantageously aids in assembly by providing a smooth engagement with the other part of the connection mechanism as described below. In another embodiment, the raised portion 72 includes a rounded edge or a radius instead of the chamfer 74 to provide similar benefits.

The raised portion 72 has a thickness 76 that spans a width, or horizontal distance of engagement, a length 78 that spans a distance along a centerline of the needle protection member 70, and a depth 79 that spans a vertical distance of engagement. The thickness 76 is minimized to satisfy overall size constraints while being large enough to provide one degree of freedom constraint in the x-axis 90.

The length 78 of the raised portion 72 is advantageously maximized to increase the mechanical advantage while adhering to overall size constraints. The length 78 also provides one degree of freedom constraint in the z-axis 94.

The depth 79 spans the vertical distance and is sized to ensure engagement with the other part of the connection mechanism for proper operation. At the same time, the depth 79 avoids interference with other features of the needle protection member 70 and/or components of the catheter assembly 10 as described below. The depth 79 also provides one degree of freedom constraint in the y-axis 92.

The distal end of the needle protection member 70 also includes a support portion 80. The support portion 80 is disposed substantially at an opposing side of the raised portion 72. The support portion 80 is disposed a bottom surface of the internal surface of the needle protection member 70. It is contemplated, however, that the support portion 80 can be located at any angular position on the internal surface of the needle protection member 70 depending on where the raised portion 72 is positioned.

The support portion 80 and the raised portion 70 limit movement of the catheter hub 30 and the needle protection member 70 in the y-axis 92 degree of freedom. Specifically, the support portion 80 keeps the depth 79 of the raised portion 70 engaged to the catheter hub 30 and helps provide a close fit. Further description of this engagement is described below.

Figure 6:
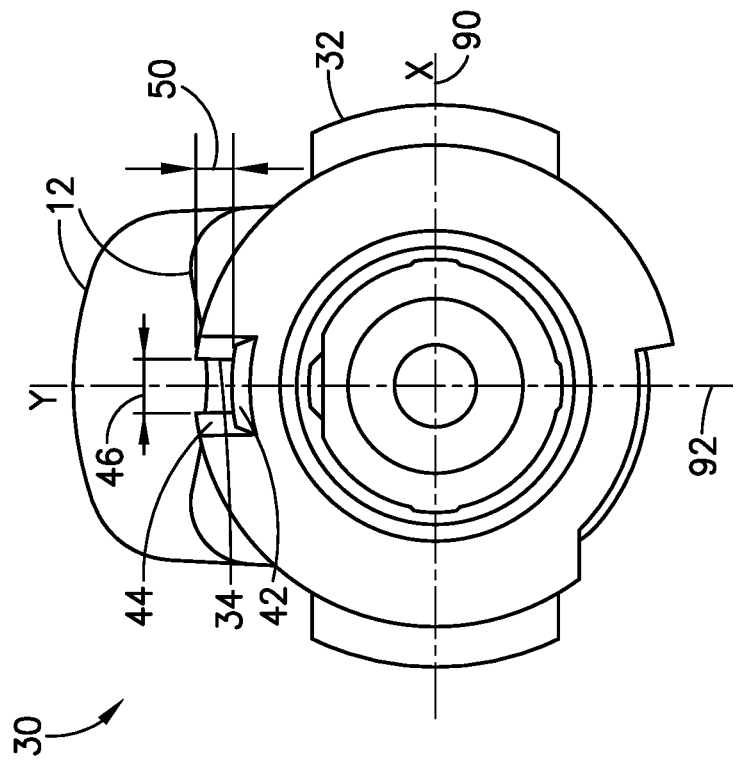
FIG. 6 illustrates a rear view of the catheter hub of FIG. 1.
Figure 7:
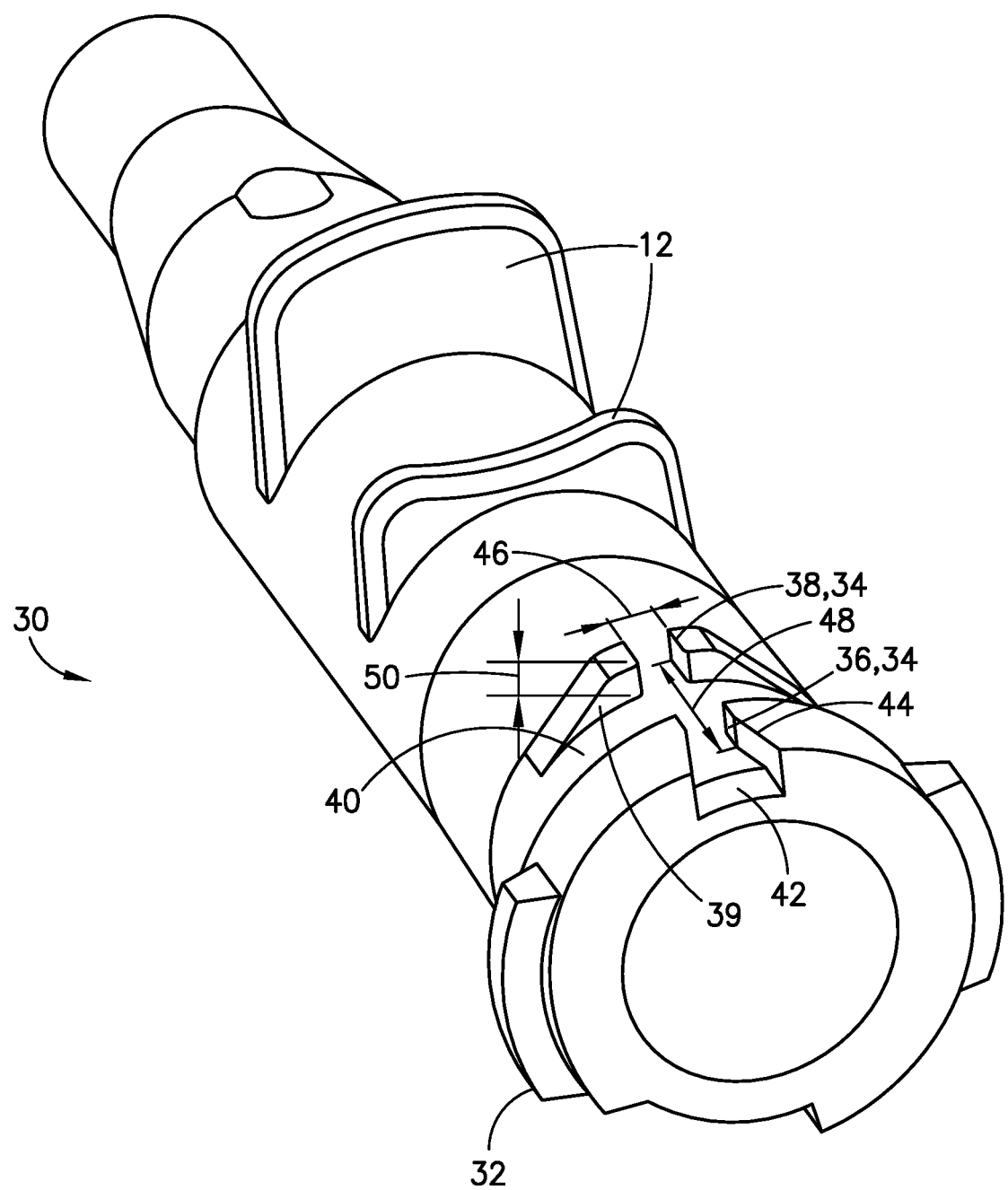
FIG. 7 illustrates a rear perspective view of the catheter hub of FIG. 6.

FIGS. 6 and 7 illustrate a channel or groove member 34 of the catheter hub 30 that provides another aspect of the connection mechanism. The channel member 34 is preferably a non-continuous groove that is disposed on an outer surface of the catheter hub 30. Specifically, the channel member 34 extends through a portion of a collar 31 at the proximal end of the catheter hub 30. The channel member 34 is advantageously recessed into the portion of the collar 31, instead of being a feature that extends beyond the height of the luer threads 32.

Thus, the connection mechanism does not increase the overall size of the catheter assembly 10. The channel member 34 is not angularly aligned to any portion of the luer threads 32 or the catheter hub 30 and does not hinder the function of the luer threads 32. Accordingly, the channel member 34 advantageously provides the connection mechanism aspect of the catheter assembly 10 while not interfering with the function of the ISO 80369-7 luer threads 32.

In another embodiment, the channel member 34 extends through a portion of the luer threads 32 of the catheter hub 30. Since only a portion of the luer threads 32 is occupied by the channel member 34, the luer threads 32 are still able to function properly.

As illustrated in FIG. 7, the channel member 34 includes a first channel 36 and a second channel 38 with a gap 40 disposed in between. The first channel 36 is disposed in the portion of the collar 31 while the second channel 38 is disposed distally to the first channel 36 and outside of the collar 31. The first and second channels 36, 38 are substantially inline.

Walls 39 are formed on the catheter hub 30 at both sides of the second channel 38. The walls 39 have heights that do not extend beyond the height of the collar 31 and the luer threads 32 to advantageously avoid any potential interference. Also, a height of the walls 39 gradually decreases via a smooth curvature to transition into the outer surface of the catheter hub 30. The transition optimizes the strength of the interface between the outer surface of the catheter hub 30 and the walls 39.

The gap 40 is provided to adequately space the first channel 36 from the second channel 38 while optimizing the mechanical advantage according to space constraint requirements. Also, the first and second channels 36, 38 are manufactured with small tolerances so that a close fit is achieved when mating with the raised portion 72 of the needle protection member 70. Although the tolerances are small, the first and second channels 36, 38 are not difficult to consistently maintain during manufacturing because of their size and shape.

Thus, the gap 40 also advantageously improves manufacturability by shortening the length of engagement of the channel member 34. Without the gap 40, it may be difficult to maintain a small and/or tight tolerance over a long length of the channel member 34. Dividing the channel member 34 via the gap 40 reduces the length at which the small and/or tight tolerances need to be held to.

The first channel 36 includes a chamfer 42 at the proximal end of the catheter hub 30. Similar to the chamfer 74 in the raised portion 72, the chamfer 42 in the first channel 36 advantageously aids in assembly by providing a gradual and smooth engagement between the needle protection member 70 and the catheter hub 30. According to another embodiment, the catheter hub 30 includes a rounded edge or a radius instead of the chamfer 42 to provide similar benefits.

The first channel 36 also includes a narrowing portion 44 at the proximal end of the catheter hub 30. The narrowing portion 44 is a V-shaped member that decreases in width from the proximal end of the catheter hub 30 and gradually transitions into the first channel 36. The narrowing portion 44 gradually tightens the connection mechanism between the catheter hub 30 and the needle protection member 70. The narrowing portion 44 advantageously aids in assembly by providing a gradual engagement between the channel member 34 and the raised portion 72 of the needle protection member 70.

The channel member 34 includes a width 46, a length 48 and a depth 50. The width 46 spans a horizontal distance of engagement. The width 46 extends through the second channel 38 and through a portion of the first channel 36. Specifically, the variable width of the first channel 36 at the narrowing portion 44 is larger than the width 46 at the remaining portion of the first channel 36.

The width 46 of the channel member 34 cooperates with the thickness 76 of the raised portion 72 to constrain the connection mechanism between the catheter hub 30 and the needle protection member 70 in the x-axis 90. Additionally, the width 46 is minimized so that the geometry of the luer sealing surface is not affected by sinks during molding. Sinks can arise when plastic shrinks after molding. The width 46 of the first channel 36 and the width 46 of the second channel 38, except for the narrowing portion 44, are substantially equal.

The length 48 of the channel member 34 spans a distance along a centerline of the catheter hub 30. The length 48 is measured from the distal end of the second channel 38 to the interface between the first channel 36 and the narrowing portion 44. This length 48 provides a long bearing surface for increased stability and one degree of freedom constraint in the z-axis 94 when the channel member 34 engages the raised portion 72. Although the length 48 of the channel member 34 includes the gap 40 between the first and second channels 36, 38, the effective bearing surface is still advantageously maintained because of the separation between the first and second channels 36, 38.

The depth 50 of the channel member 34 spans the vertical distance of engagement. The depth 50 provides an engagement surface between the raised portion 72 of the needle protection member 70 and the catheter hub 30. Also, the depth 50 provides one degree of freedom constraint in the y-axis 92. The depth 50 of the first channel 36 and the depth 50 of the second channel 38 are substantially equal.

In another embodiment, the channel member 34 and the raised portion 72 is a tapered tongue and groove feature. Specifically, the raised portion 72 increases in depth 79 from the distal end of the needle protection member 70 to the end of the raised portion 72. Likewise, the channel member 34 increases in depth 50 from the proximal end of the catheter hub 30 to the end of the second channel 38. In another embodiment, the raised portion 72 decreases in depth 79 from the distal end of the needle protection member 70 to the end of the raised portion 72. Likewise, the channel member 34 decreases in depth 50 from the proximal end of the catheter hub 30 to the end of the second channel 38. Accordingly, in both these embodiments, the channel member 34 and the raised portion 72 complement each other when fully assembled to provide similar disclosed benefits to the catheter assembly 10 as described herein.

Figure 10:
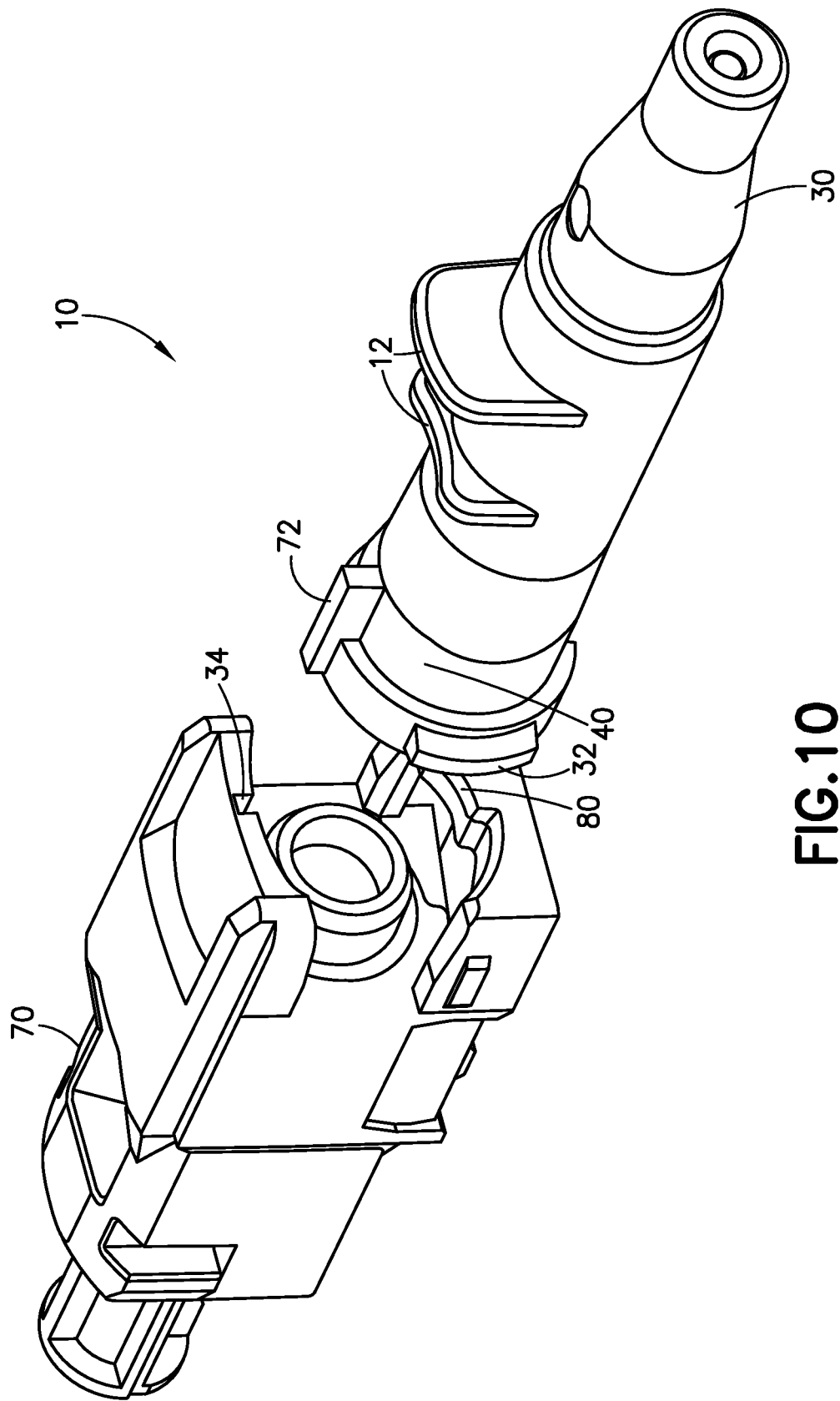
FIG. 10 illustrates a partial assembly view of an alternate embodiment of the catheter assembly of FIG. 1.

According to another embodiment, as illustrated in FIG. 10, the raised portion 72 is disposed on the catheter hub 30 and the channel member 34 is disposed on the needle protection member 70. Accordingly, the connection mechanism features are reversed to provide similar function and advantages. Further, alternate connection mechanism geometry can be used to limit deflection or gain similar functionality.

Figure 8:
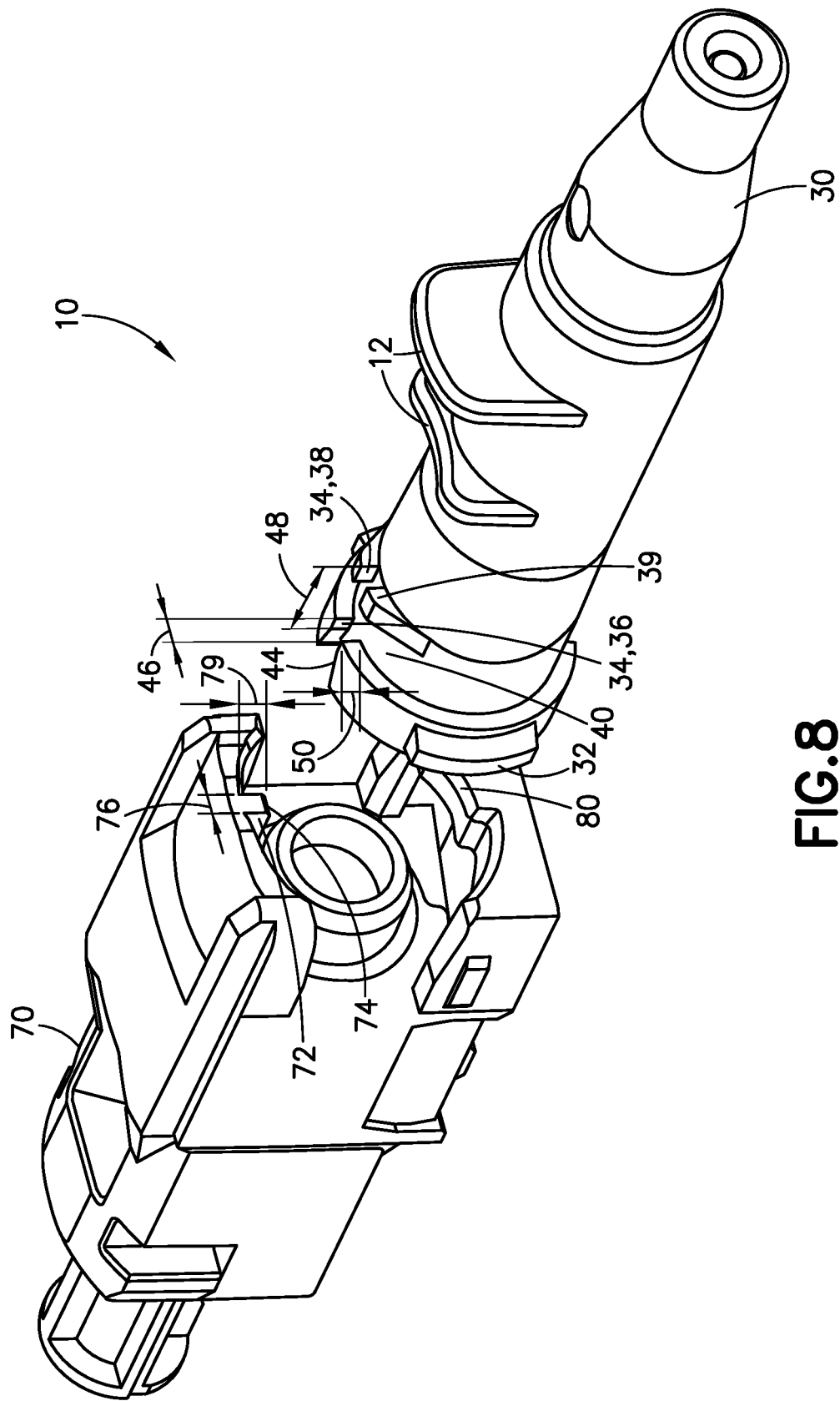
FIG. 8 illustrates a partial disassembled view of the catheter assembly of FIG. 1.
Figure 9:
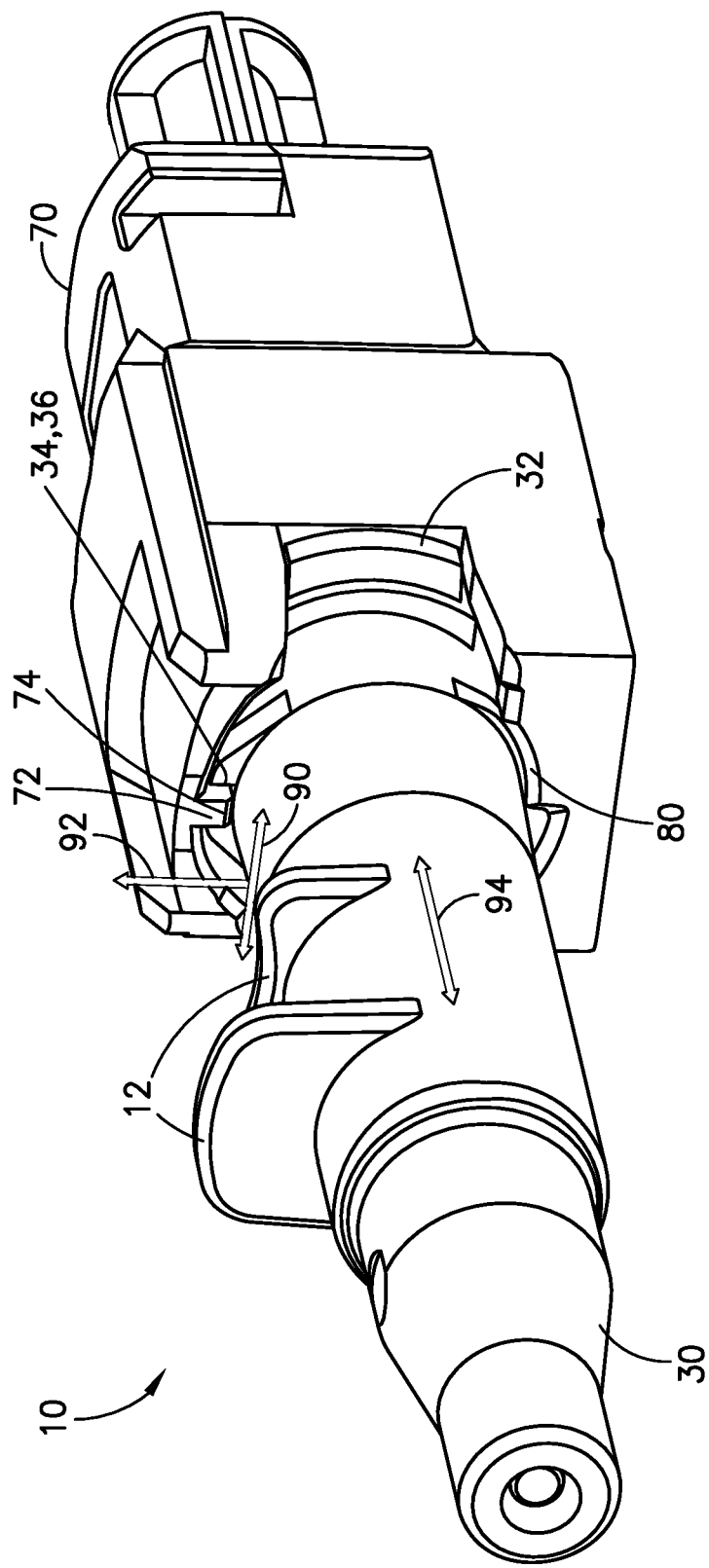
FIG. 9 illustrates a partial assembly view of the catheter assembly of FIG. 1.

FIGS. 8 and 9 illustrate the connection mechanism between the catheter hub 30 and the needle protection member 70 during assembly and after the assembly is secured. The connection mechanism grips and constrains the catheter hub 30 and the collar 31 to the needle protection member 70. This provides passive safety to the clinician and improves the success of vascular access.

Specifically, as the distal end of the needle protection member 70 is drawn toward the proximal end of the catheter hub 30, the raised portion 72 is aligned to the channel member 34. The chamfer 74 on the raised portion 72 first engages the chamfer 42 and the narrowing portion 44 of the catheter hub 30 to advantageously provide smooth and gradual engagement.

At the same time, the support portion 80 engages the outer surface of the catheter hub 30 to provide further restricted movement in the y-axis 92. As the catheter hub 30 travels further into the needle protection member 70, the raised portion 72 continues to engage the first channel 34 and subsequently the second channel 36.

The assembly of the needle protection member 70 and the catheter hub 30 is performed as a manufacturing subassembly process. The clinician is not involved in this subassembly process. The clinician only separates the needle protection member 70 from the catheter hub 30 after the catheter assembly 10 is used.

FIG. 9 illustrates the catheter hub 30 fully engaged to the needle protection member 70. In this position, the spring clip 66 engages the collar 31 to lock the catheter hub 30 to the needle protection member 70. The width 46 and the length 48 of the catheter hub 30 engaging the thickness 76 and the length 78 of the needle protection member 70 advantageously secures the catheter assembly 10 at one degree of freedom in the x-axis 90.

The depth 50 of the channel member 34 engaging the depth 79 of the raised portion 72, as well as the opposing support portion 80 in the needle protection member 70, advantageously secures the catheter assembly 10 at one degree of freedom in the y-axis 92. Thus, the lateral movement in the x-axis 90 and the radial movement in the y-axis 92 between the catheter hub 30 and the needle protection member 70 are restricted. On the other hand, the transverse motion in the z direction 94 between the catheter hub 30 and the needle protection member 70 is still permitted.

The connection mechanism between the catheter hub 30 and the needle protection member 70 as described provides little to no support at the internal diameter of the catheter hub 30. Nevertheless, the connection mechanism provides a significant benefit to the catheter assembly 10 based on a simple geometry, relatively small features and improved manufacturability. The catheter hub 30 is constrained by the needle protection member 70 to minimize motion. Specifically, the length 78 of the needle protection member 70 and the length 48 of the catheter hub 30 provide improved stability during insertion by the clinician while reducing deflection in the catheter assembly 10. The improved rigidity provides the clinician greater control.

The connection mechanism advantageously does not require tight tolerances which would impair manufacturability. Moreover, the connection mechanism is not a large feature that is difficult to manufacture and does not increase the length or height of the catheter assembly 10. That is, there are no large features in the catheter hub 30 that extend around the exterior of the luer threads 32. These advantages including the advantages described above provide an improved catheter assembly 10 for the clinician to operate.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they don't contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A catheter assembly comprising:
   a catheter;
   a needle having a distal tip and disposed within the catheter;
   a catheter hub connected to the catheter having the needle passing therethrough; and
   a housing attachable to the catheter hub, wherein
   an external surface of the catheter hub includes one of a channel member and a raised portion;
   an internal surface of the housing includes an other of the channel member and the raised portion that extends radially inward from the internal surface of the housing such that the channel member and the raised portion are engaged to restrict motion between the catheter hub and the housing, the raised portion being a rigid member; and
   the channel member includes a first channel and a second channel separated by a gap, each of the first channel, the second channel and the gap are longitudinally aligned along the catheter such that the gap is distal to the first channel and the second channel is distal to the gap to restrict the motion between the catheter hub and the housing when the channel member is engaged to the raised portion.

2. The catheter assembly of claim 1, wherein
   the internal surface of the housing includes the raised portion; and
   the raised portion does not extend beyond a distal surface of the housing.

3. The catheter assembly of claim 1, wherein a distal end of the raised portion includes a chamfer.

4. The catheter assembly of claim 1, wherein the raised portion has a thickness, a length and a depth.

5. The catheter assembly of claim 1, wherein a distal end of the housing includes a support portion disposed at a substantially opposing side surface of the raised portion.

6. The catheter assembly of claim 5, wherein the support portion and the raised portion limit movement of the catheter hub and the housing in at least one axis of freedom.

7. The catheter assembly of claim 1, wherein
   a proximal end of the external surface of the catheter hub includes the channel member;
   the first channel narrows in width in a distal direction; and
   the channel member is disposed in a radially outward protruding rim.

8. The catheter assembly of claim 7, wherein the first channel includes a chamfer to aid in engaging the raised portion.

9. The catheter assembly of claim 1, wherein the first channel includes a narrowing portion that gradually tightens the engagement between the channel member and the raised portion.

10. The catheter assembly of claim 1, wherein the channel member has a width, a length and a depth.

11. The catheter assembly of claim 1, wherein
    the first channel and the second channel are longitudinally aligned and each of the first channel and the second channel has a width, a length and a depth; and
    a depth of the gap is equal to the depth of the first channel.

12. The catheter assembly of claim 11, wherein
    the width of the first channel is substantially equal to the width of the second channel;
    the depth of the first channel is substantially equal to the depth of the second channel;
    the length of the first channel is greater than the width of the first channel; and
    the length of the second channel is greater than the width of the second channel.

13. The catheter assembly of claim 1, wherein the first channel and the second channel limit at least rotational movement of the catheter hub with respect to the housing in at least one axis of freedom.

14. The catheter assembly of claim 1, wherein
    the catheter hub includes luer threads and a collar, and
    the channel member and the raised portion do not interfere with operation of the luer threads.

15. The catheter assembly of claim 14, wherein the channel member extends through a portion of the collar or a portion of the luer threads.

16. The catheter assembly of claim 1, wherein the housing comprises a needle protection member that encloses the distal tip of the needle.

17. The catheter assembly of claim 1, wherein the housing comprises a needle hub.

18. The catheter assembly of claim 1, wherein the housing comprises a grip.

* * * * *